United States Patent [19]

Oppenlaender et al.

[11] 4,438,094

[45] Mar. 20, 1984

[54] COSMETIC FORMULATIONS CONTAINING OXYETHYLATED DIPHENYLAMINES AS SUN SCREEN AGENTS

[75] Inventors: Knut Oppenlaender, Ludwigshafen; Rainer Strickler, Heidelberg; Karl Seib, Weinheim; Paul Naegele, Neuhofen, all of Fed. Rep. of Germany

[73] Assignee: BASF Aktiengesellschaft, Ludwigshafen, Fed. Rep. of Germany

[21] Appl. No.: 373,417

[22] Filed: Apr. 30, 1982

[30] Foreign Application Priority Data

May 15, 1981 [DE] Fed. Rep. of Germany ....... 3119385

[51] Int. Cl.$^3$ .......................... A61K 7/42; A61K 7/035
[52] U.S. Cl. ........................................... 424/59; 8/405; 424/60; 424/69; 424/174; 524/246
[58] Field of Search ..................... 424/60, 59

[56] References Cited

U.S. PATENT DOCUMENTS

| | | | |
|---|---|---|---|
| 3,683,020 | 8/1972 | Luethi | 424/60 |
| 4,009,254 | 2/1977 | Renold | 424/60 |
| 4,200,432 | 4/1980 | Kalopissis et al. | 8/408 |

FOREIGN PATENT DOCUMENTS

| | | | |
|---|---|---|---|
| 3007997 | 9/1981 | Fed. Rep. of Germany | 424/62 |
| 951538 | 4/1949 | France | 8/408 |
| 1276771 | 6/1972 | United Kingdom | 8/407 |

*Primary Examiner*—Dale R. Ore
*Attorney, Agent, or Firm*—Joseph D. Michaels; David L. Hedden

[57] ABSTRACT

Cosmetic preparations are prepared containing from 0.1 percent to 15 percent by weight of oxyethylated diphenylamines as sun screen agents.

4 Claims, No Drawings

COSMETIC FORMULATIONS CONTAINING OXYETHYLATED DIPHENYLAMINES AS SUN SCREEN AGENTS

BACKGROUND OF THE INVENTION

1. Field of the Invention

The invention relates to the use of oxyethylated diphenylamines as sun screen agents in cosmetic preparations.

2. Description of the Prior Art

It is known that the range of sunlight or artificial light sources between 280 and 320 nm referred to as ultraviolet-B-radiation is responsible for the formation for erythema of the human skin. The maximum effectiveness of the ultraviolet radiation for the formation of erythema lies at 297 nm if the radiation intensity is equal for all wave lengths. In the case of sunlight with radiation of varying intensity, this maximum shifts to 308 nm. By using suitable filter substances for the ultraviolet-B range, it is possible to prevent or at least delay the formation of erythema. The pigment formation of the skin that is tanning should, however, be retained.

In addition, ultraviolet radiation is an important influencing factor in the aging of polymers and may, for instance, cause degradation of certain dyestuffs so that filter substances are almost essential as stabilizers for such products.

During the past forty years, a great number of chemical compounds has been examined for their filtering effects in the ultraviolet-B range. Whether or not a substance absorbs light in the ultraviolet range and is also a usable sun screen for the human skin is determined by several factors. In addition to the high filtering effectiveness in the erythemal range, the substance should have a relatively high permeability in the ultraviolet-A range. It should also be as compatible with the skin and the mucous membrane and must not be toxic. Finally the substance should not be sensitive to oxidation and should not be altered or discolored by ultraviolet radiation. A preparation containing the substance should be storage stable, should not have an intrinsic odor, and should be compatible with commonly used cosmetic ingredients.

The known ultraviolet screening substances frequently have the drawbacks that they are unstable to ultraviolet radiation or visible radiation and/or air during storage, that they are transformed into colored decomposition products, that they soil clothing, or that they can even damage the skin. In practice, relatively few substances, which more or less meet the listed requirements have become accepted as is indicated, for instance, in *Chemische Rundschau* 24, (1971) page 1097.

It is known from German Pat. No. 1,543,387, that polyalkoxylated para-aminobenzoates can be used as sun screen agents. The polyalkoxylation is carried out by reacting the corresponding carboxylic acids or carboxylates with alkylene oxides in the presence of an alkaline catalyst. The alkylene oxides may be added to the carboxylic acid or to the amino group.

SUMMARY OF THE INVENTION

The present invention relates to the use of N-oxyethylated diphenylamines as sun screen agents in cosmetic formulations. More particularly, the invention relates to a cosmetic preparation comprising a carrier, auxiliary agents and from 0.1 percent to 15 percent by weight, based on the total weight of the preparation, of an N-oxyethylated diphenylamine sun screen agent.

DESCRIPTION OF THE PREFERRED EMBODIMENT

The N-oxyethylated diphenylamines of use in the present invention have been oxyethylated 1–25 fold, preferably 5–15 fold. The ethoxylates to be used in accordance with this invention can be prepared in a simple fashion from easily accessible ingredients. In the first step, diphenylamine is preferably reacted with ethylene oxide in the presence of an acid catalyst, preferably a Lewis acid such as zinc chloride, aluminum chloride, or iron-III chloride at temperatures between 70° and 160° C. and pressures between 1 and 10 bars. This reaction is known from a publication in *Liebigs Annalen der Chemie*, 725, pages 222 to 225 (1969). The resulting N-(2-hydroxyethyl-diphenylamine is useful in the present invention. It is advantageous, however, to further react these compounds.

The N-(2-hydroxyethyl)-diphenylamine can be reacted in a conventional manner with ethylene oxide to result in higher oxyethylated products. The N-hydroxyethyldiphenylamine can be reacted with ethylene oxide in a commonly used fashion to result in higher oxyethylated products. Catalysts for the oxyethylation are hydroxides, alcoholates, or oxides of elements of the first and second main groups of the periodic system, particularly, sodium or potassium, which are used in accordance with well known methods. The reaction is preferably carried out at temperatures between 80° C. and 160° C. in the presence of preferably 0.1 percent to 5 percent by weight of the catalyst and under pressures between 1 and 10 bars. The reaction times are generally 1 hour to 20 hours preferably 4 hours to 8 hours. The course of the oxyethylation can be monitored by commonly used analytical methods. These methods are well known and therefore do not require specific information at this point.

The end of the reaction can be recognized by the fact that no further pressure reduction and thus no further ethylene oxide absorption takes place at the same temperature. At the end of the reaction process, after cooling of the mixture, the alkaline reaction agents may be neutralized by adding dilute carboxylic acid while stirring.

The compounds to be used in accordance with this invention absorb the ultraviolet-B range with a very good degree of extinction. By varying the degree of oxyethylation, compounds of a certain consistency and with desired properties relative to the solubility can be produced. An advantage of these compounds lies in the fact that they are relatively water soluble, particularly when the compounds contain more than six oxyethylene groups hereinafter referred to as oxyethylation degrees.

Diphenylamines with oxyethylation degrees of less than 6 show a good solubility in alcohols, natural and synthetic esters, and other cosmetic based materials. Thus, the physical properties can be individually adjusted by the degree of oxyethylation. A particular advantage consists of the fact that the compounds used are not saponifiable and thus have a high chemical stability. Due to their chemical structure, they further have surfactant properties which facilitates additional stabilization of cosmetic formulations and emulsions.

High sun screen factors can be achieved with these compounds. The filtering effect for the ultraviolet-B range in aqueous solution can generally be used for stabilizing cosmetic preparations, plastics, dyestuffs, solvents, or coatings. They may also be used in combination with other sun screens. According to this invention, cosmetic preparations or formulations generally contain 0.1 percent to 15 percent of these compounds. Percentages of 2 percent to 8 percent by weight represent particularly preferred ranges. Otherwise, the cosmetic preparations contain the commonly used solid, semi-solid, or liquid carriers, or dilution agents, mixtures thereof, and other commonly used cosmetic auxiliaries.

It depends upon the type of the carrier, the auxiliaries, or diluting agents whether or not the completed preparation containing the sun screen is a solution, an oil, a cream, a salve, a lotion, a gel, or a powder. Such preparations are described, for instance, in "*Fette und Seifen,*" [Fats and Soaps] volume 53, pages 694 to 699 (1951), "*Seifen, Oele, Fette, Wachse,*" [Soaps, Oils, Fats, Waxes] 1955, page 147, or H. Janistyn, Handbuch der Kosmetika und Riechstoffe, [*Handbook of Cosmetics and Fragrances,* volume 3 (1973)].

Commonly used cosmetic auxiliaries, which are suitable additives, include emulsifiers such as fatty alcohol ethoxylates, fatty ester of Sorbitan, or lanolin derivatives, thickeners such as carboxymethyl cellulose, or crosslinked polyacrylic acid, preservatives or fragrances. Examples for basis for tanning oils with sun screens include vegetable oils such as peanut oils, olive oil, sesame oil, cottonseed oil, coconut oil, grape kernel oil, castor oil, or mineral oils such as Vaseline oil, or particularly liquid paraffin, esters of synthetic fatty acids and glycerides.

Base materials for soaps include Vaseline, lanolin, Eucerin, or polyethylene glycol. Base materials for creams include high fat creams such as glycerine cream, polysaccharide cream, Tylose cream, and for creams based on fats and waxes ethyl alcohol, lanolin cream, coco butter, beeswax, stearic acid, stearyl alcohol, glycerine monostearate, native or mineral oil and fats present suitable basis.

Base materials for emulsions include mixtures of stearyl glycol, a vegetable and/or mineral oil such as almond oil, paraffin oil, and Vaseline and water or mixtures of ethyl alcohol, water, lanolin and Tragant, or mixtures of ethyl alcohol, stearin, water or Tragant, glycerine, alcohol and water, or mixtures of stearic acid, paraffin oil, propyl or isopropyl alcohol and water.

For stabilizing plastics, dyestuffs, and other light sensitive industrial products, the products to be used in accordance with this invention are generally added to the respective substances by mixing in amounts of 0.1 percent to 5 percent by weight.

The examples following explain the invention without restricting it. All parts are by weight unless otherwise indicated.

EXAMPLE 1

In a 0.5 liter V$_2$A mixing autoclave, 169.1 parts of diphenyl amine (1 mole) and 6.76 parts (49 millimole; 4 percent by weight based on diphenyl amine) of anhydrous zinc chloride are added and 46.2 parts of ethylene oxide (1.05 mole) are thereafter passed into the autoclave at 110° C. under nitrogen pressure (maximum pressure 6 bar). Following this process, the mixture is stirred at 110° C. for three hours. After a completed reaction (pressure drop by 2.5 to 3 bar/constant pressure for three hours) the reaction product is distilled by applying an oil pump vacuum. The resultant product, 185.3 parts, is (87 percent) of N-(2-hydroxyethyl)-diphenyl amine as clear light yellow at viscous oil having a boiling point of 0.15 137° to 139° C.

($n_D^{20} = 1.6205$; $d_4^{20} = 1.1204$; $\eta 20 - 598.4$ cP).

$^1$H-NMR-Spectrum (CDCl$_3$)$\delta = 2.85$ (s) ppm (1 proton) $\delta = 3.65$ (t) ppm (4 protons) $\delta = 6.98$ (m) ppm (10 protons).

C$_{14}$H$_{15}$NO calculated: C 78.83 H 7.09 N 6.57 found: C 78.80 H 7.20 N 6.60.

EXAMPLES 2 TO 8

In a V$_2$A autoclave under N$_2$ padding are placed 213 parts (1 mole) of N-(2-hydroxyethyl)-diphenylamine (according to example 1) and 1.065 parts (0.5 percent by weight) of KOH powder. Thereafter, ethylene oxide (see table) is charged in batches at temperatures of 110° C. to 120° C. Addition time varies from 4 to 6 hours at 6 bars. Post addition period is 2 hours. The products prepared are described in Table I.

TABLE I

| Example Number | Moles of Ethylene Oxide Charged | Moles of Ethylene Oxide Added | Product Characteristics | | | Maximum ε(1000 cm$^2$) Mole |
|---|---|---|---|---|---|---|
| | | | Amount Weighed (g) (Theory) | OH Number (Theory) | UV-Spectrum: X (nm) | |
| 2 | 5.0 | 176 g (4 mole) | 358 g (389) | 136 (144) | 298.5 | 11410 |
| 3 | 7.0 | 264 g (6 mole) | 467 g (477) | 112.5 (118) | 298.3 | 11004 |
| 4 | 10.0 | 396 g (9 mole) | 594 g (609) | 90 (92) | 299.1 | 11169 |
| 5 | 12.8 | 519 g (11.8 mole) | 719 g (732) | 75 (77) | 298.0 | 11029 |
| 6 | 15.0 | 616 g (14 mole) | 816 g (829) | 72 (68) | 298.3 | 11408 |
| 7 | 17.5 | 726 g (16.5 mole) | 923 g (939) | 69 (60) | 298.0 | 11688 |
| 8 | 21.2 | 889 g (20.2 mole) | 1087 g (1102) | 52 (51) | 297.8 | 11587 |

EXAMPLE 9

Preparation of an oil-in-water sun screen cream with the product of Example 4.

| Part(s) | Formulation Ingredient |
|---|---|
| 7.0 | glycerine monostearate |
| 2.0 | cetyl alcohol |

| Part(s) | Formulation Ingredient |
|---|---|
| 2.0 | Cotyl ®-(stearyl alcohol + 25 moles EO) |
| 2.0 | Cotyl ®-(stearyl alcohol + 25 moles EO) |
| 4.0 | paraffin oil |
| 4.0 | fatty acid triglyceride |
| 5.0 | product of Example 4 |
| 3.0 | 1,2-propylene glycol |
| 0.5 | preservative |
| 0.2 | fragrance oil |
| 70.3 | water |

EXAMPLE 10

Preparation of a sun screen gel with product of Example 5.

| Parts | Formulation Ingredient |
|---|---|
| 5.0 | product of Example 5 |
| 1.0 | 40-fold oxyethylated hydrogenated castor oil |
| 15.0 | ethanol |
| 0.8 | polyacrylic acid |
| 1.0 | triethanolamine |
| 0.2 | fragrance oil |
| 77.0 | water |

EXAMPLE 11

Water-in-oil sun screen creams with N-(2-hydroxyethyl)-diphenylamine.

| Part(s) | Ingredient |
|---|---|
| | Formulation A |
| 10.0 | paraffin oil |
| 10.0 | isopropyl myristate |
| 3.0 | N—(2-hydroxyethyl)-diphenyl amine |
| 3.0 | Sorbitan sesquioleate |
| 1.0 | aluminum stearate |
| 1.0 | magnesium stearate |
| 5.0 | micro crystalline wax |
| 3.0 | 1,2-propylene glycol |
| 0.5 | preservative |
| 0.2 | fragrance oil |
| 63.3 | water |
| | Formulation B |
| 20.0 | Vaseline |

| Part(s) | Ingredient |
|---|---|
| 5.0 | peanut oil |
| 5.0 | isopropyl myristate |
| 3.0 | Sorbitan sesquioleate |
| 3.0 | N—(2-hydroxyethyl)-diphenylamine |
| 4.0 | micro crystalline wax |
| 1.5 | calcium stearate |
| 3.0 | glycerine |
| 0.5 | preservative |
| 0.2 | fragrance oil |
| 54.8 | water |

The embodiments of the invention in which an exclusive privilege or property is claimed are defined as follows:

1. A sunscreen composition comprising from 0.1 percent to 15 percent, based upon the total weight of the composition, of an N-oxyethylated diphenylamine sunscreen agent of the formula

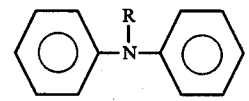

wherein R is $(CH_2-CH_2-O)_n-H$ and n is an integer from 1 to 25, a cosmetic carrier selected from the group consisting of a solution, an oil, a cream, a salve, a lotion, a gel and a powder and auxiliary agents selected from the group consisting of thickeners, emulsifiers, preservatives and fragrances.

2. The preparation of claim 1 wherein the diphenylamine is N-(2-hydroxyethyl)-diphenylamine.

3. The prepartion of claim 1 wherein the N-oxyethylated diphenylamine sun screen agent is a 5 to 15 mole ethylene oxide adduct of diphenylamine.

4. A sun screen composition comprising from 1 percent to 15 percent by weight, based on the total weight of the composition, of an N-oxyethylated diphenylamine of the formula

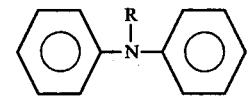

wherein R is $(CH_2-CH_2-CH_2-O)H$ and n is an integer from 1 to 25.

* * * * *

UNITED STATES PATENT AND TRADEMARK OFFICE
CERTIFICATE OF CORRECTION

PATENT NO. : 4,438,094
DATED : March 20, 1984
INVENTOR(S) : Knut Oppenlaender, Rainer Strickler, Karl Seib and Paul Naegele It is certified that error appears in the above-identified patent and that said Letters Patent is hereby corrected as shown below:

Column 6, Claim 4, line 6, change $(CH_2-CH_2-CH_2-O)H$ to "$(CH_2-CH_2-O)H$".

Signed and Sealed this

Seventh Day of August 1984

[SEAL]

Attest:

Attesting Officer

GERALD J. MOSSINGHOFF

Commissioner of Patents and Trademarks